(12) United States Patent
Farjot et al.

(10) Patent No.: US 11,717,635 B2
(45) Date of Patent: Aug. 8, 2023

(54) ARGON COMBINED WITH THROMBECTOMY IN THE EVENT OF ISCHAEMIC STROKE

(71) Applicants: L'Air Liquide, Société Anonyme pour l'Etude et l'Exploitation des Procédés Georges Claude, Paris (FR); Aix-Marseille Universite, Marseilles (FR); Centre National de la Recherche Scientifique, Paris (FR)

(72) Inventors: Géraldine Farjot, Les Loges en Josas (FR); Catherine Billoet, Gentilly (FR); Lionel Velly, Marseilles (FR); Thomas Brochier, Marseilles (FR)

(73) Assignees: L'Air Liquide, SociétéAnonyme pour l'Etude et l'Exploitation des Procédés Georges Claude, Paris (FR); Aix-Marseille Université, Marseilles (FR); Centre National de la Recherche Scientifique, Paris (FR)

( * ) Notice: Subject to any disclaimer, the term of this patent is extended or adjusted under 35 U.S.C. 154(b) by 379 days.

(21) Appl. No.: 17/018,311

(22) Filed: Sep. 11, 2020

(65) Prior Publication Data
US 2021/0077767 A1 Mar. 18, 2021

(30) Foreign Application Priority Data
Sep. 12, 2019 (FR) ...................................... 1910063

(51) Int. Cl.
*A61M 16/12* (2006.01)
*A61B 17/22* (2006.01)
*A61K 9/00* (2006.01)
*A61P 9/10* (2006.01)
(Continued)

(52) U.S. Cl.
CPC ............. *A61M 16/12* (2013.01); *A61B 17/22* (2013.01); *A61K 9/0073* (2013.01); *A61K 33/00* (2013.01);
(Continued)

(58) Field of Classification Search
CPC .............. A61M 16/12; A61M 2202/02; A61M 2202/0208; A61M 2202/0241;
(Continued)

(56) References Cited

U.S. PATENT DOCUMENTS

| | | | |
|---|---|---|---|
| 2002/0115081 A1* | 8/2002 | Lee ........................... | A61P 9/04 514/18.9 |
| 2005/0152988 A1 | 7/2005 | Lemaire et al. | |

(Continued)

FOREIGN PATENT DOCUMENTS

| | | |
|---|---|---|
| EP | 0 424 550 | 5/1991 |
| EP | 1 541 156 | 6/2005 |

(Continued)

OTHER PUBLICATIONS

Gardner, A.J. et al., Moving to human trials for argon neuroprotection in neurological injury: a narrative review, British Journal of Anaesthesia, 2018, 120 (3): 453-468.
(Continued)

*Primary Examiner* — Joseph D. Boecker
(74) *Attorney, Agent, or Firm* — Allen E. White

(57) ABSTRACT

The invention relates to an inhalable gaseous medicament containing argon gas for use in combination with a mechanical thrombectomy for treating, reducing or resorbing brain lesions subsequent to an ischaemic stroke in an individual. Preferably, the proportion by volume of argon is between 30 and 79%. The mechanical thrombectomy can be accompanied by a drug-based thrombolysis to dissolve the clot and to thin the blood of the patient.

13 Claims, 1 Drawing Sheet

(51) Int. Cl.
*A61K 33/00* (2006.01)
*A61P 7/02* (2006.01)

(52) U.S. Cl.
CPC .................. *A61P 7/02* (2018.01); *A61P 9/10* (2018.01); *A61B 2017/22084* (2013.01); *A61M 2202/02* (2013.01); *A61M 2202/0208* (2013.01); *A61M 2202/0241* (2013.01); *A61M 2205/05* (2013.01)

(58) Field of Classification Search
CPC ..... A61M 2205/05; A61P 9/0073; A61P 9/10; A61B 2017/22084; A61K 33/00
See application file for complete search history.

(56) References Cited

U.S. PATENT DOCUMENTS

2010/0278942 A1* 11/2010 Abraini .................. A61P 7/02
424/600
2017/0312460 A1* 11/2017 Riess .................. A61M 16/12
2020/0171078 A1* 6/2020 David .................. A61K 33/00

FOREIGN PATENT DOCUMENTS

WO  WO 2008 132239      11/2008
WO  WO-2010035074 A1 *  4/2010  ............ A61K 33/00

OTHER PUBLICATIONS

Ma, S. et al., Argon inhalation for 24 hours after onset of permanent focal cerebral ischemia in rats provides neuroprotection and improves neurologic outcome, Critical Care Medicine, Aug. 2019, vol. 47, No. 8, e693-e699.

French Search Report for corresponding FR 1910063, dated May 14, 2020.

* cited by examiner

[Fig. 1]
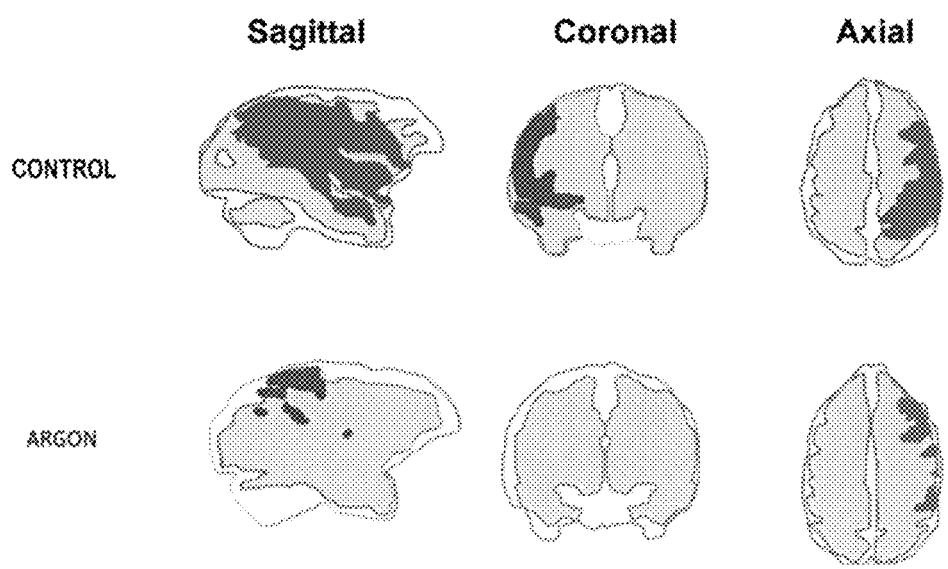
[Fig. 2]
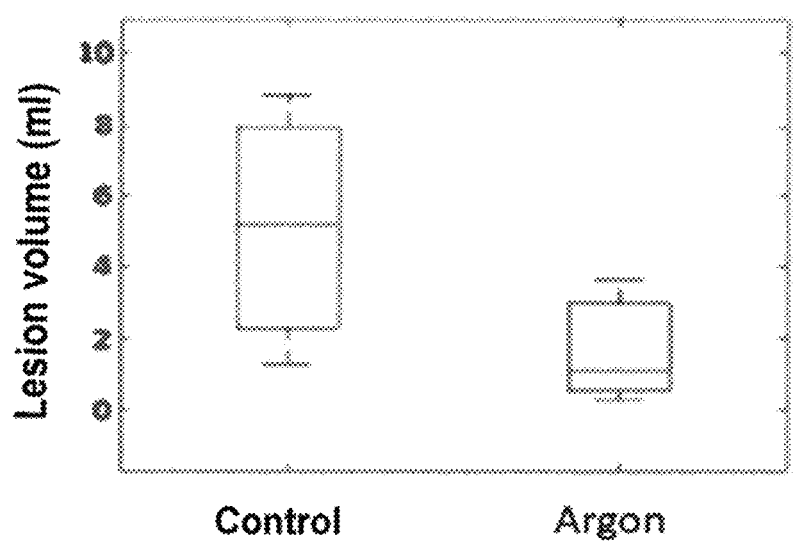

ARGON COMBINED WITH THROMBECTOMY IN THE EVENT OF ISCHAEMIC STROKE

CROSS REFERENCE TO RELATED APPLICATIONS

This application claims the benefit of priority under 35 U.S.C. § 119 (a) and (b) to French Patent Application No. 1910063, filed Sep. 12, 2019, the entire contents of which are incorporated herein by reference.

BACKGROUND

The present invention relates to an inhalable gaseous medicament containing argon gas, in particular a binary mixture of argon and oxygen, for use in combination with a mechanical thrombectomy for treating, reducing or resorbing brain lesions subsequent to an ischaemic stroke in an individual, i.e. a patient.

Ischaemic stroke is a major cause of morbidity-mortality. Furthermore, neurological and functional recovery after an ischaemic stroke is often incomplete. Thus, after 1 year, half of survivors suffer to varying degrees from motor and mental pathological conditions. Ischaemic stroke is worldwide the first cause of disability in adults and the third cause of mortality.

The majority of ischaemic strokes are due to a blood clot which blocks a blood vessel in the brain of an individual, thereby blocking the blood flow, and therefore the irrigation and oxygenation of a brain region, resulting in weakening and then death of the neurons in the non-irrigated area.

This damage occurs immediately during a stroke, but also after a stroke, that is to say that it spreads during the subsequent hours and days, despite the resolving of the clot by mechanical thrombectomy, that is to say a mechanical extraction of the clot, by thrombolytic agents which bring about a pharmacological dissolution of the clot, or by means of these two methods combined together.

Mechanical thrombectomy, by allowing rapid removal of the blood clot, has greatly improved, compared with thrombolysis alone, the post-stroke prognosis. However, less than half of patients get over a stroke with a clinical score that allows them to live autonomously 90 days after the stroke, and a large majority of them suffer from after effects, or even die in the aftermath of the treatment.

The objective of all the current treatments for stroke is to restore the cerebral flow. In other words, none of the existing treatments treat the brain cells weakened by the consequences of stroke, in particular lack of oxygen, inflammation, oedema, oxidative stress, etc.

Moreover, there are studies relating to the protective effects of argon on various in vitro and in vivo models of brain cell attack. However, those which studied the effects of exposure to argon in the context of a cerebral ischaemia were carried out in experimental rodent models which poorly reproduce the human conditions of ischaemic stroke and which have never given rise to the slightest medicament placed on the market.

This is explained by the fact that these rodent models have shown their limits for reproducing human brain function and the pathological human condition. Indeed, the structural and functional differences between a human brain and a rodent brain are too great and, in fact, at the current time, no treatment of cells weakened by cerebral ischaemia having demonstrated an effect in rodents has reproduced its effect in human beings. In other words, the observations made in rodents are not transposable to human beings in this pathological condition, in particular with regard to the precise modes of use and of dosage regimen of a new treatment.

In view of that, one problem is that of being able to improve the treatment of ischaemic strokes in human beings in such a way as to treat, reduce or resorb brain lesions subsequent to such an ischaemic stroke.

SUMMARY

A solution according to the invention relates to an inhalable gaseous medicament containing argon gas for use in combination with a mechanical thrombectomy for treating, reducing or resorbing brain lesions subsequent to an ischaemic stroke in an individual, i.e. a human being.

In other words, the invention relates to an inhalable gaseous medicament containing argon gas for use in a method for treating, reducing or resorbing brain lesions subsequent to an ischaemic stroke in an individual who must subsequently undergo a mechanical thrombectomy, said method comprising:
  (a) the administration of the gaseous medicament by inhalation after said ischaemic stroke,
  (b) followed by a mechanical thrombectomy with mechanical extraction of at least one portion of the blood clot resulting from the ischaemic stroke, and in which the administration of the gaseous medicament by inhalation:
  i) is begun as early as possible after an ischaemic stroke diagnosis, and
  ii) is maintained throughout the thrombectomy.

It is preferentially continued after the mechanical thrombectomy, that is to say after reperfusion.

The gaseous medicament is therefore in a form suitable for administration by inhalation in a patient who must subsequently undergo a mechanical thrombectomy for the purpose of eliminating all or part of the blood clot associated with the ischaemic stroke, the administration of the gaseous medicament beginning after the ischaemic stroke, in particular after diagnosis, i.e. confirmation, of the ischaemic stroke and before the beginning of the mechanical thrombectomy and is continued during the mechanical thrombectomy and preferentially also after the mechanical thrombectomy, that is to say after reperfusion.

Depending on the embodiment taken into consideration, the gaseous medicament of the invention may comprise one or more of the following features:
  it contains an effective proportion by volume of argon;
  argon is the active ingredient of the medicament;
  the proportion by volume of argon is between 30 and 79%;
  the proportion by volume of argon is between 40 and 70%;
  the proportion by volume of argon is between 50 and 65%;
  the argon is mixed with a gas containing at least 21% by volume of oxygen, preferably at least 30% of oxygen (% by vol.);
  the gaseous argon is mixed with 35 to 50% of oxygen;
  it is formed of a binary mixture of argon and oxygen;
  it is formed of a binary mixture of argon and oxygen, in which the proportion by volume of argon is approximately equal to 60% and the proportion by volume of oxygen is equal to 40%;

it does not contain xenon;

it is in a form suitable for administration by inhalation before, during and/or after the mechanical thrombectomy;

it is in a form suitable for administration inhaled via the nasal, buccal or pharyngeal route, including the nasal-pharyngeal route;

it is in a form suitable for administration by inhalation as soon as possible after an ischaemic stroke diagnosis, that is to say within the minute or minutes which follow the ischaemic stroke diagnosis so as to avoid worsening the ischaemic stroke. The faster the administration is carried out, that is to say without delaying, the more the harmful effects of the ischaemic stroke in the patient can be reduced, i.e. limited or minimized;

it is in a form suitable for administration by inhalation after the mechanical thrombectomy, that is to say that it is maintained after several minutes or tens of minutes after the reperfusion subsequent to the thrombectomy, preferably for at least 10 minutes, more preferably for at least 15 to 20 minutes, advantageously for at least 30 minutes, and even up to at least 60 minutes, or even longer, after reperfusion;

the individual is an adult, an adolescent or a child;

the individual is an adult at least 40 years old, preferably at least 50 years old;

it is combined with a mechanical thrombectomy with or without drug-based thrombolysis, that is to say with optional administration of a medicinal agent for thinning the blood and for breaking up at least a portion of the clot;

the proportion of argon is chosen in order to act efficaciously on the brain cells of the penumbral area that have been weakened by the ischaemic stroke;

the proportion of argon is chosen in order to improve the neuronal plasticity of the brain cells of the penumbral area;

the brain lesions are of inflammation, blood-brain barrier rupture, cell apoptosis, tissue necrosis, oedema, or the like, type;

the mechanical thrombectomy comprises a mechanical extraction of the blood clot by means of a catheter inserted into a blood vessel, in particular an artery;

the method for treating, reducing or resorbing the brain lesions subsequent to the ischaemic stroke comprises sedation of the patient at least during the mechanical thrombectomy, that is to say that the mechanical thrombectomy is performed on a patient under general anaesthesia or local anaesthesia, preferably combined with conscious sedation;

the method for treating, reducing or resorbing the brain lesions subsequent to the ischaemic stroke comprises sedation of the patient by administration of one or more sedative, analgesic or anaesthetic products, for example halothane, isoflurane, desflurane, sevoflurane, thiopental, propofol, fentanyl, midazolam, propofol, remifentanyl, or the like;

the gaseous medicament is packaged in a pressurized gas container, in particular a pressurized gas cylinder;

the gas from the pressurized gas container is administered to the patient via inhalation via the nasal, buccal or pharyngeal, i.e. tracheal, route, including the nasobuccal route, by means of a suitable respiratory interface, such as a mask, nasal cannulas or a tracheal tube for example;

the gaseous medicament from the pressurized gas container is administered to the patient by means of a medical device for administering gas, that is to say either a valve suitable for spontaneous respiration of the gaseous medicament, or an assisted ventilation device (or medical ventilator) which supplies the patient with gaseous medicament, preferably via a suitable respiratory interface fluidically connected to the medical device for administering gas, by means of a flexible pipe or the like.

The method for administering argon to an individual, i.e. a patient, with an ischaemic stroke is for example the following:

a) a 60% Ar/40% $O_2$ (% by vol.) mixture is inhaled by means of a breathing device suitable for nasal, buccal or tracheal administration, for example a breathing mask or a tracheal tube, to a patient immediately after confirmation of the stroke diagnosis by brain imaging, for example of scanner (CT) or MRI type;

b) the administration by inhalation of the $Ar/O_2$ mixture is continued throughout the preparation of a mechanical thrombectomy procedure, typically for approximately 15 to 45 minutes, and during the mechanical thrombectomy procedure per se, as described above; and c) preferably, the administration by inhalation of the $Ar/O_2$ mixture is stopped after the mechanical thrombectomy procedure, that is to say after the removal of the clot by means of a catheter, preferably several minutes after the thrombectomy, preferentially at least 10 to 15 minutes after reperfusion, more preferably between 10 and 60 minutes after reperfusion, typically approximately 30 minutes after reperfusion.

Preferably, the mechanical thrombectomy procedure is accompanied by, i.e. is combined with, a drug-based thrombolysis with administration of a medicinal agent for thinning the blood and breaking up the clot.

Moreover, the mechanical thrombectomy procedure is carried out with general or local anaesthesia (e.g. locoregional anaesthesia) or conscious sedation of the patient.

BRIEF DESCRIPTION OF THE DRAWINGS

The invention will now be better understood by virtue of the following detailed description from a study in rhesus macaque monkeys, which is given by way of non-limiting illustration, and with reference to the appended figures, in which:

FIG. 1 schematically represents infarcted volumes (dark grey) compared to the volumes of white matter (light grey), from MRI images in sagittal, coronal and axial views of the brains of a representative animal of the "argon group" and of a representative animal of the "control group"; and FIG. 2 represents the distribution of the lesion volumes in the "control group" and the "argon group".

DETAILED DESCRIPTION OF PREFERRED EMBODIMENTS

Contrary to rodent models, non-human primates have a gyrencephalic brain structure, a vascular and microvascular architecture, and coagulation and homeostatic regulation systems that are very similar to those of human beings. As a result, in the context of the present invention, a primate model is used since it constitutes an ideal model for accurately exploring the clinical conditions of the treatment of ischaemic stroke.

Such a primate model has never previously been used to study ischaemic stroke treatment, that is to say to attempt to find an effective means for treating, reducing or resorbing all or part of the brain lesions subsequent to an ischaemic stroke in human beings.

The primates used in the study are rhesus macaques, in which it has been possible to obtain a stable and reproducible model of reversible ischaemia mimicking an ischaemic stroke and its reperfusion by mechanical thrombectomy, as explained below.

After approval of the project by the ethics committee for animal experimentation, 6 rhesus macaques were randomized in 2 groups of 3 animals per group, namely:

a group treated with argon or "argon group" inhaling, for 90 min in total, a binary gas mixture formed of 60% argon and 40% oxygen (vol. %), the inhalation of the gas beginning 30 min after the start of the ischaemia and extending during and after the thrombectomy procedure (with or without thrombolysis);

a "control group" inhaling a gas mixture formed of 60% nitrogen and 40% oxygen (vol. %).

These groups are subjected to a model of transient focal cerebral ischaemia without craniectomy consisting of an occlusion under anaesthesia of the middle cerebral artery (MCA) by deploying a rigid microspring, called a "microcoil", until the arterial blood flow stops, in the M2 segment of the right MCA.

After 90 min of ischaemia, which is the usual average time between the first signs of an ischaemic stroke and the cerebral reperfusion, the "microcoil" was removed and the revascularization confirmed by arteriography. This procedure mimics a blood clot and its removal by mechanical thrombectomy.

All the animals are monitored by high-resolution MRI (Prisma 3 Tesla, Siemens) several days before and directly after the ischaemia (3D-T1, 3D-T2, 3D-FLAIR, DTI, TOF) in order to quantify the cerebral volume made ischaemic (i.e. restriction of the apparent diffusion coefficient) and the cerebral oedema (i.e. T2-FLAIR).

Moreover, the functional recovery was monitored in the acute phase in 1 control animal and over the long-term in two animals of the argon group, that is to say over the course of 3 months post-ischaemia. The evaluations were carried out in terms of the clinical and functional neurological recovery with behavioural tests evaluating their fine sensory-motor performances.

The results obtained, which can be seen in FIG. 1 and FIG. 2, show that the cerebral ischaemia carried out on the primate model caused a cerebral infarction volume of 5.4±3.3 cm$^3$, encompassing all of the parietal lobe and extending to the temporal and frontal lobes of the primates of the "control group".

In the "argon group", the exposure to inhaled argon led to a significant decrease in the cerebral volume infarcted (i.e. 83% reduction; P<0.05) and in the volume of cerebral oedema (i.e. 85% reduction; P<0.05) compared to the "control group". Thus, the lesion volume is about 5 ml in the "control group", but only about 1 ml in the "argon group".

On the MRI images, a rupture of the blood-brain barrier, which is a known phenomenon during stroke in human beings, was also observed in the animals of the "control group", whereas the blood-brain barrier was preserved in the animals of the "argon group".

In other words, argon preserves the blood-brain barrier during stroke and therefore protects the brain against damage that this rupture could cause.

In behavioural terms, the animals of the "argon group" treated by inhalation of argon and monitored long term (i.e. 3 months) exhibited a rapid recovery with only a minor and transient neurological deficit post-ischaemia, namely left leg paresis. Their performances in the behavioural tests were not significantly impaired post-ischaemia compared with the baseline data.

In the "control group" animal, recovery was slow, or even non-existent, with persistence of more or less significant neurological deficits.

These results show that the inhaled argon makes it possible to treat the brain cells weakened during post-stroke ischaemia and therefore to reduce the extent and the final volume of the brain lesions of such a stroke, after reperfusion by means of a mechanical thrombectomy, that is to say administered during and after a procedure to resolve the ischaemic stroke by mechanical thrombectomy, with or without thrombolysis, aimed at eliminating the blood clot that has formed and that caused the stroke.

More specifically, the argon makes it possible to improve the neuronal plasticity in the penumbral area, that is to say in the area of the cells weakened by the cerebral ischaemia, when the ischaemic stroke event is resolved in a few hours by a mechanical thrombectomy with or without thrombolysis.

In other words, the argon treats the neurological deficit and allows, moreover, an accelerated recovery and therefore a faster return to normal life.

These results obtained in a primate model can be extrapolated to human beings, contrary to those obtained in rodents.

Given these observations, it is preferable to begin the administration of argon by inhalation as soon as possible after the diagnosis and throughout the procedure for resolving the stroke, that is to say during the mechanical thrombectomy, with or without thrombolysis, and also for at least 30 minutes after the reperfusion following the elimination of the blood clot.

The argon is in a mixture with oxygen or co-administered with oxygen. Advantageously, an $Ar/O_2$ mixture containing approximately 60% of argon and 40% of oxygen is used, given that this dose was demonstrated as effective while at the same time making it possible to maintain an oxygenation compatible with the vital needs of the individual treated.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method for treating, reducing or resorbing brain lesions subsequent to an ischaemic stroke in an individual who subsequently undergoes a mechanical thrombectomy, said method comprising:
    (a) administering a gaseous medicament containing Argon by inhalation after said ischaemic stroke,
    (b) followed by performing the mechanical thrombectomy with a mechanical extraction of at least one portion of a blood clot resulting from the ischaemic stroke, and in which the administration of the gaseous medicament containing Argon by inhalation:
    i) is begun after an ischaemic stroke diagnosis, and
    ii) is maintained throughout the thrombectomy,
characterized in that the gaseous medicament containing Argon is greater than 50% by volume Argon.

2. The method according to claim 1, characterized in that the gaseous medicament containing Argon is mixed with a gas containing at least 21% by volume of oxygen.

3. The method according to claim 2, characterized in that the gaseous medicament containing Argon is mixed with a gas containing 35 to 50% of oxygen.

4. The method according to claim 3, characterized in that a final proportion by volume of Argon is equal to 60% and the proportion by volume of oxygen is equal to 40%.

5. The method according to claim 1, characterized in that the gaseous medicament containing Argon is in a form suitable for inhaled administration by the nasal, buccal or pharyngeal route.

6. The method according to claim 1, characterized in that the administration of the gaseous medicament containing Argon by inhalation is continued after a reperfusion subsequent to the mechanical extraction of the at least one portion of the blood clot resulting from the ischaemic stroke.

7. The method according to claim 6, characterized in that the administration of the gaseous medicament containing Argon by inhalation is continued for at least 30 minutes after reperfusion.

8. The method according to claim 1, characterized in that the gaseous medicament containing Argon is packaged in a pressurized gas container.

9. The method according to claim 1, characterized in that the individual is an adult, an adolescent or a child.

10. The method according to claim 1, characterized in that the mechanical thrombectomy comprises the mechanical extraction of the entire blood clot resulting from the ischaemic stroke.

11. The method according to claim 1, characterized in that the mechanical thrombectomy is combined with a drug-based thrombolysis.

12. The method according to claim 1, characterized in that the method comprises a step of confirming an ischaemic stroke diagnosis by brain imaging prior to step (a).

13. The method according to claim 1, characterized in that the method comprises administering an anaesthetic to the individual.

\* \* \* \* \*